United States Patent [19]

Lemelson

[11] 4,273,123
[45] Jun. 16, 1981

[54] SYRINGE AND NEEDLE COVER

[76] Inventor: Jerome H. Lemelson, 85 Rector St., Metuchen, N.J. 08840

[21] Appl. No.: 80,561

[22] Filed: Oct. 1, 1979

[51] Int. Cl.³ .............................................. A61M 5/00
[52] U.S. Cl. ................................ 128/218 N; 128/221
[58] Field of Search ............... 128/218 N, 218 R, 215, 128/221; 206/365

[56] References Cited

U.S. PATENT DOCUMENTS

| | | | |
|---|---|---|---|
| 3,008,570 | 11/1961 | Roehr et al. | 128/218 N |
| 3,021,942 | 2/1962 | Hamilton | 128/218 N X |
| 3,320,954 | 5/1967 | Cowley | 128/218 N X |
| 3,796,359 | 3/1974 | Dick | 206/365 |

FOREIGN PATENT DOCUMENTS 2611448  3/1977  Fed. Rep. of Germany ...... 128/218 N

*Primary Examiner*—John D. Yasko

[57] ABSTRACT

A protective closure for the needle of a hypodermic syringe, which closure is also operable to receive and retain such needle after it is removed from or broken off the end of the syringe. In one form, the retainer is in the form of a cylinder with a closed outer end and a neck adapted to frictionally fit against a portion of the end of the syringe to protect its needle during storage prior to use. The closed end of the closure contains a tubular formation protruding therein for receiving the needle of the syringe which penetrates the bottom wall of the tubular formation. Once the needle is removed or broken off the syringe, it is retained by friction within the closure so that it may be disposed of without posing a hazard. In another form, a narrow tubular formation is integrally molded at one side of the closure and contains a partition therein through which the needle of the syringe may be penetrated and retained thereby within the tubular formation for disposal without posing a hazard.

6 Claims, 6 Drawing Figures

U.S. Patent　　　　Jun. 16, 1981　　　　4,273,123

SYRINGE AND NEEDLE COVER

SUMMARY OF THE INVENTION

This invention relates to a unique syringe assembly including a closure in the form of an elongated tubular protective cap which frictionally assembles to the end of a medical syringe to protect the needle thereof from dirt and contamination prior to its use. The closure is injection molded of a suitable plastic material and is such a shape that, when its closed end is properly aligned with the needle of the syringe from which the closure is removed, it may be utilized to receive the syringe needle and either effect or assist in breakage or removal of the needle from the syringe and retain same within or adjacent the closure to prevent the needle from inflicting injury to a person handling the used syringe or garbage in which said syringe is disposed.

Heretofore, it has been the practice of physicians and nurses who employ hypodermic syringes for injecting medication into the skin, tissue or muscle or a person, to either dispose disposable syringes in a garbage container or bag or to break off the needle from the body of the syringe in order to prevent injury or possible infection to persons handling the syringe or garbage thereafter. This procedure generally leaves the needle exposed and it must be picked up and disposed in a garbage container which still defines a hazard.

The instant invention is directed to simple structures in closures which frictionally assemble to the ends of disposable hypodermic syringes, surround and protect the hypodermic needles thereof. Such closures are injection molded to plastic resin and are formed with tubular formations containing partitions or wall portions adapted to be penetrated and pierced by the hypodermic needle so that, after such needle is removed from or broken off the syringe, it will be retained within the closure or a side formation thereof so that it may be dispensed without posing a hazard to a person handling the remains of the disposable syringe.

Accordingly it is a primary object of this invention to provide a new and improved closure for the needle of a hypodermic syringe.

Another object is to provide a hypodermic syringe closure which may be utilized to receive and retain a spent or used hypodermic needle for disposing same without posing a hazard.

Another object is to provide a hypodermic syringe and a closure for protecting the needle thereof which closure may also be utilized to facilitate breaking a needle from the syringe.

With the above and such other objects in view, the invention consists of the novel structures, constructions and arrangement of parts as will hereafter more fully appear in the specification and accompanying drawings but it is to be understood that changes, variations and modifications may be resorted to without departing from the spirit and nature of the invention.

Figure 1:
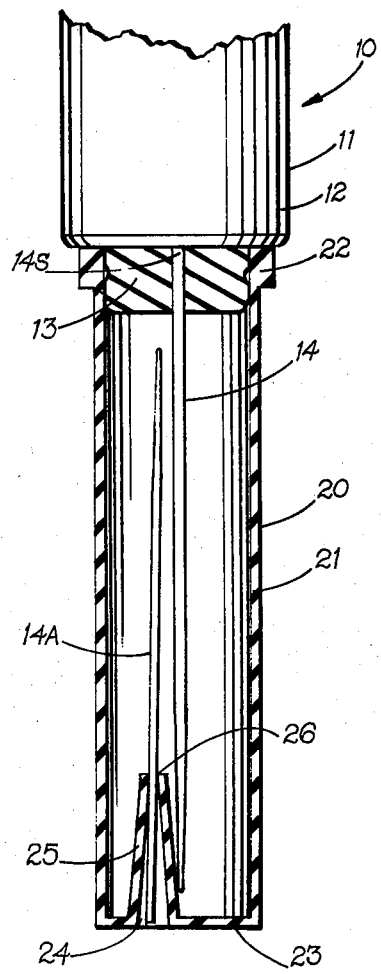
FIG. 1 is a partial side view with parts broken away and sectioned for clarity of the working end of a hypodermic syringe and a protective closure for the needle thereof, which closure may also be utilized to receive and retain the needle of the syringe after it has been broken off its support at the end of the syringe.

In FIG. 1 is shown a portion of an assembly 10 including a hypodermic syringe body 11 formed with an upper cylindrical side wall 12 and a protruding nose or end wall 13 containing a hypodermic needle 14 frictionally secured or bond welded to the central opening in syringe portion 13.

The closure 20 is an elongated tubular formation formed by injection molding and having an end wall 23 in which is molded a tapered tubular formation 25 which protrudes a short distance upwardly into the volume defined by the cylindrical side wall 21 and the end wall 23 of the device 20.

In FIG. 1 is shown as assembly 10 including a portion of the cylindrical housing 12 of a disposable hypodermic syringe 11 and an elongated protective closure 20 for the needle 14 of the syringe. The closure 20 is molded of a plastic resin and is formed with a cylindrical side wall 21 and a closed end wall 23. The other end of the elongated closure 20 is open and is formed with a neck portion 22 containing a circular groove or cavity 22C molded therein which receives a circular beaded formation 13B surrounding the nose end formation 13 at the end of the cylindrical housing 12, which formation retains the end of the needle 14 which passes therethrough and has its other end communicating with the interior of the syringe cylinder 12.

Integrally molded in the end wall 23 of the closure 20 is an inwardly extending tapered conical formation 25 having a pierceable end wall 26 disposed within the volume interior of the closure 20 and defining an elongated cavity 24 into which the end of the needle 14 may be inserted and guided after the hypodermic syringe has been used when it is desired to dispose of the syringe. When so inserted and pushed through the end wall 26 for most of its length, the needle may be broken from the end portion thereof supported by the nose formation 13, by bending such needle against the side wall of tubular formation 25 while such side wall is held by hand or is disposed against a surface such as a table top. In FIG. 1, a broken needle 14A is shown inserted in and held by the tubular formation 25 as a result of its frictional retention in the pierced end wall thereof.

Figure 1A:
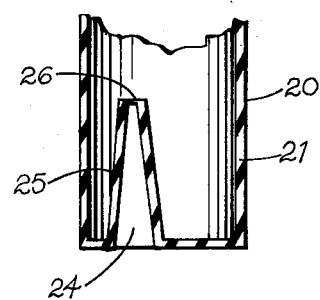
FIG. 1A is a side view in cross section of the lower end of FIG. 1 showing further details of the retainer for the needle.

FIG. 1A shows the end of closure 20 before the needle 14 is inserted into the cavity 24. Notation 14S refers to a scribed or machined groove circumscribing the needle 14 at the location thereof where it is desired to break the end of the needle off as described .

Figure 3:
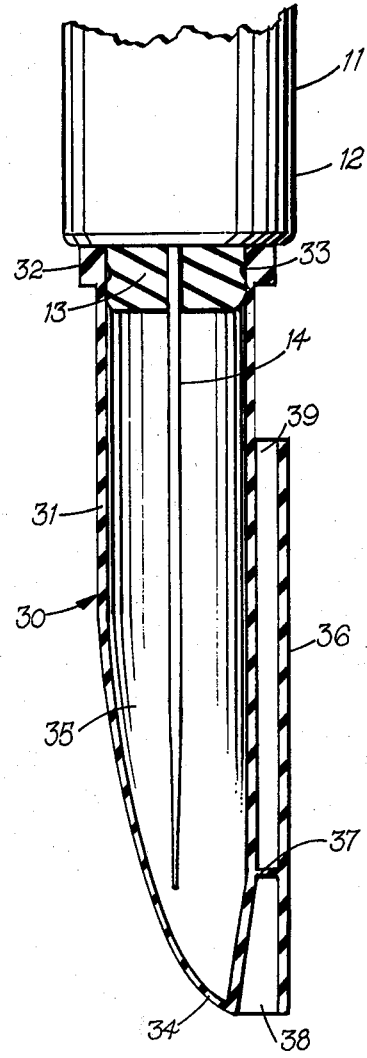
FIG. 3 is a side view with parts broken away and sectioned of another type of hypodermic syringe having a closure for protecting its needle which closure is formed with an exterior tubular portion for receiving and retaining the broken needle.

In FIG. 3, an assembly 10A including the described hypodermic syringe 11 with the nose end 13 thereof frictionally retaining a closure and having a tapered side wall 31 surrounding and enclosing the hypodermic needle 14 which is attached at its other end to the nose end 13 of the syringe and passes therethrough to the interior of the syringe cylinder. The open end of the closure 30 has a neck formation 32 which is molded integral with the side wall 31 for frictionally retaining such closure against the nose end 13 of the syringe and such side wall 31 has an elongated tubular formation 36 molded integral therewith which tubular formation is opened at both ends.

Figure 4:
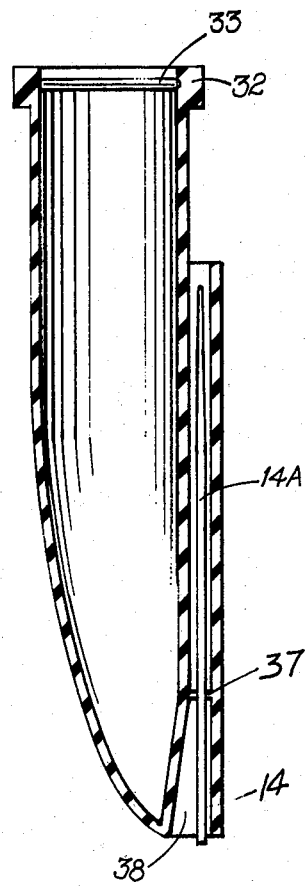
FIG. 4 shows further details in cross section of the closure of FIG. 3.
Figure 2:
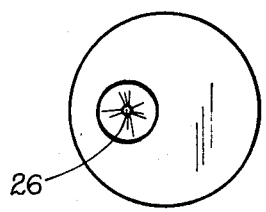

Formed intermediate the ends of tubular formation 36 of the plastic forming the entire closure 30 is a thin partition 37 capable of receiving and of being penetrated by the needle 14 when it is inserted into the cavity 38 defined by the conically tapered lower end of the tubular formation and also serves to retain the broken needle 14A therein as shown in FIG. 4.

Figure 5:
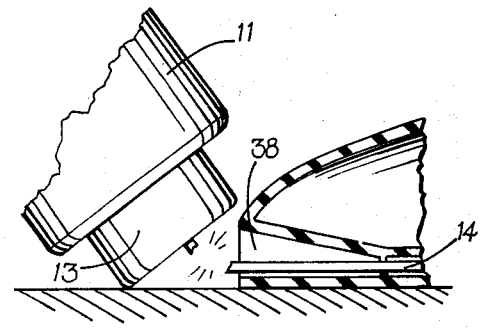
FIG. 5 is a partial side view in cross section of a portion of a hypodermic syringe including the needle thereof after it has been inserted into the exterior tubular formation of the closure of FIG. 3 and is being bent to effect a breakage in the needle within a portion of the closure.

In FIG. 4 the hypodermic needle 14 is shown broken broken from the synringe body, preferably by the procedure illustrated in FIG. 5 by causing the needle to penetrate the partition 37 after inserting it into the passageway or cavity 38 at the far end of the closure or cover 30 and thereafter effecting a bending torque or movement between such closure 30 and the body 11 of the syringe either by holding both in both hands and exerting a bending force therebetween or by placing the closure on a surface such as a table top and exerting and upward bending force on the syringe by hand until the needle breaks off at or near the nose portion 13 of the syringe leaving the broken portion 14A of the needle within the passageway 38 as shown. Tubular formation 36 of the closure or cover 30 is preferably of such a length as to prevent the end of the broken off needle 14A from protruding beyond the end of such formation, which end may also be closed off.

Notation 33 refers to a shallow channel molded in the neck 32 at the upper end of the cover 30 into which channel a circular beaded formation molded in the nose end portion 13 of the hypodermic syringe 11 frictionally engages to frictionally hold the cover in assembly with the syringe as shown in FIG. 3.

The closures or protective covers 20 and 30 of FIGS. 1 and 3 are preferably injection molded of a suitable plastic resin such as polyethylene or polypropylene which may deform for frictional assembly with the end of the syringe and which may be penetrated without difficulty and frictionally hold the broken needle as described and illustrated.

I claim:

1. A disposable hypodermic syringe comprising in combination:
   a tubular housing which is open at one end and closed at the other,
   a hypodermic needle secured to the closed end of said housing,
   a piston slidably movable within the interior of said tubular housing for forcing a liquid therefrom through said hypodermic needle,
   a protective plastic closure of elongated tubular shape open at one end and closed at the other,
   said closure adapted to surround said hypodermic needle and to be frictionally engaged within the end of the tubular housing supporting said needle to provide protection for said needle during storage of the syringe,
   said closure having a thin wall portion containing a tubular extension thereof defining a passageway for receiving said needle, and
   a penetrable wall extending across said tubular extension through which penetrable wall said needle may be passed after penetrating same so as to permit said needle to be frictionally held within said tubular extension and to be retained therein after the syringe and needle have been used.

2. A hypodermic syringe in accordance with claim 1 wherein said tubular extension is formed in the end of said closure.

3. A hypodermic syringe in accordance with claim 2 wherein said penetrable wall of said tubular extrusion is operable to frictionally hold said needle to permit said needle to be broken adjacent where it is secured to said syringe while so held and to permit the broken portion of the needle to be retained within said tubular extension by said thin wall portion.

4. A hypodermic syringe in accordance with claim 3 wherein the hypodermic needle is weakened in the area where it is secured to the body of the syringe permitting it to be broken while retained by said penetrable wall portion within said tubular extension.

5. A hypodermic syringe in accordance with claim 1 wherein said tubular extension is formed with a circumscribing side wall which protrudes into the interior of the closure.

6. A hypodermic syringe in accordance with claim 1 wherein said tubular extension is formed with a side wall which extends exterior of the main wall of said closure.

* * * * *